(12) United States Patent
Ockert

(10) Patent No.: US 6,417,184 B1
(45) Date of Patent: Jul. 9, 2002

(54) TRIPLE DRUG THERAPY FOR THE TREATMENT AND PREVENTION OF ACUTE OR CHRONIC PAIN

(76) Inventor: David M. Ockert, 145 E. 32$^{nd}$ St., Sixth Floor, New York, NY (US) 10016

( * ) Notice: Subject to any disclaimer, the term of this patent is extended or adjusted under 35 U.S.C. 154(b) by 0 days.

(21) Appl. No.: 09/932,293

(22) Filed: Aug. 17, 2001

Related U.S. Application Data

(60) Provisional application No. 60/233,518, filed on Sep. 19, 2000.

(51) Int. Cl.$^7$ .................. A61K 31/55; A61K 31/52; A61K 31/445; A61K 31/42; A61K 31/415
(52) U.S. Cl. ................ 514/221; 514/220; 514/264; 514/317; 514/376; 514/392; 514/401; 514/561; 514/567; 514/617; 514/618; 514/634; 514/654
(58) Field of Search ................ 514/220, 221, 514/264, 317, 376, 401, 392, 561, 567, 617, 618, 634, 654

(56) References Cited

PUBLICATIONS

Voigtlander et al, Derwent Drug File Abstracts, abstract No. 1983–41541, 1982.*

* cited by examiner

*Primary Examiner*—William R. A. Jarvis
(74) *Attorney, Agent, or Firm*—Price, Heneveld, Cooper, DeWitt & Litton

(57) ABSTRACT

A triple drug therapy, pharmaceutical kit, composition, and method of treatment regimen utilized as a combination of effective amounts of an anxiolytic agent, centrally acting alpha antiadrenergic agent, and central nervous system stimulant for the reduction or prevention of dizziness, drowsiness, depression, delirium, lethargy, mania, orthostatic hypotension, restlessness, weakness in the extremities, and difficulty in being mobile negative side effects caused by therapeutic agents utilized in the treatment of acute and chronic pain syndromes.

67 Claims, 1 Drawing Sheet

TRIPLE DRUG THERAPY FOR THE TREATMENT AND PREVENTION OF ACUTE OR CHRONIC PAIN

CROSS-REFERENCE TO RELATED APPLICATION

This application claims priority under 35 U.S.C. §119(e) on U.S. Provisional Application No. 60/233,518, filed Sep. 19, 2000, the entire disclosure of which is incorporated herein by reference.

BACKGROUND OF THE INVENTION

1. Field of the Invention

The present invention relates to the treatment and prevention of acute or chronic pain syndromes.

2. Description of the Related Art/Background Information

Pain sensation is complex and variable. Experiences considered painful by one subject may not be equally painful to another and may vary in the same subject depending on the circumstances presented. In addition, subjective experiences, i.e. "phantom limb pain" make it clear that there is a strong psychological component to pain. Wingard et al., *Human Pharmacology: Molecular to Clinical*, Mosby-Year Book, Inc., 1991, p. 383.

Several groups of compounds are used to relieve pain, depending on the severity and duration of the pain sensation, and on the nature of the painful stimulus. Drugs used to relieve mild, moderate or severe pain without causing unconsciousness are generally called analgesics. Mild analgesics that are termed non-narcotic agents include aspirin, acetaminophen and non-steroidal anti-inflammatory drugs. Should non-narcotic based agents prove ineffective, narcotic/opioid analgesic agents such as morphine, codeine, meperidine, and the like are used to treat more severe acute or chronic forms of pain. Ibid., pp. 383, 391–92.

Generally, there are two different types of nociceptive (noxious) stimuli, which are intense enough to be perceived as pain within the human body and can be alleviated by narcotic and non-narcotic analgesic agents. One type, somatic pain, consists of an intense, localized, sharp or stinging sensation. Somatic pain is believed to be mediated by fast-conducting lightly myelinated A-delta fibers that have a high threshold (i.e. require a strong mechanical stimulus to sense pain) and enter into the spinal cord through the dorsal horn of the central nervous system where they terminate mostly in lamina I of the spinal cord. Ibid., p. 383.

The second type of pain, sometimes referred to as visceral pain, is characterized as a diffuse, dull, aching or burning sensation. Visceral pain is believed to be mediated largely by unmyelinated, slower-conducting C-fibers that are polymodal (i.e., mediate mechanical, thermal, or chemical stimuli). C-fibers also enter the spinal cord through the dorsal horn of the central nervous system where they terminate mostly in the outer layer of lamina II of the spinal cord. Ibid., p. 383. Both somatic and visceral pain can be sensed centrally and peripherally within the human body.

Central sensitization, i.e. central pain, takes place within the dorsal horn of the spinal cord, the brain stem, and brain. Amplification of nociceptive input in the spinal cord produces secondary hyperalgesia around the site of injury once central sensitization has begun. Central sensitization is believed to be evoked by A-beta low-threshold mechanoreceptors. Often, central sensitization is initiated by slow synaptic potentials through A-delta and C fibers within the dorsal horn of the central nervous system. The long duration of these slow potentials permit summation of potentials during repetitive nociceptor input and generates progressively greater and longer-lasting depolarization in dorsal horn neurons. Several seconds of C fiber input results in several minutes of postsynaptic depolarization.

This depolarization is believed to result from the activation of N-methyl-D-aspartic acid (NMDA) receptors like glutamate, and activation of the NK-1 tachykinin receptor by substance P and neurokinin A. Activation of these receptors allows an inrush of calcium through ligand and voltage-gated ion channels and activation of guanosine triphosphate (GTP) binding proteins. "Pain and Memory", *Pain Clinical Updates*, Vol. VII, Iss. 1, Spring 1999, p. 2. These second messengers in turn simulate protein kinase C activity, which enhances the function of ion channels and intracellular enzymes by phosphorylating proteins. Ibid., p. 3.

Another mechanism of central sensitization involves the production of intracellular nitric oxide. It has been proposed that activation of the NMDA receptor leads to an influx of calcium ion, which activates a central enzyme nitric oxide synthetase. Intracellular nitric oxide release stimulates transduction of protein kinase C, increases the effects of glutamate, and may interfere with the release of inhibitory neurotransmitters from inhibitory neurons within the central nervous system, causing increases in pain in both the acute and chronic syndromes. Nitric oxide antagonism is therefore another strategy to prevent central sensitization. Ibid., p. 3.

Peripheral sensitization, i.e. peripheral pain, is generally caused by activating A-delta and C nociceptors. Peripheral sensitization is induced by neurohumoral alterations at the site of injury to the human body and surrounding tissue area. Biochemicals released by tissue injury, such as potassium, prostaglandins, bradykinin, and the like excite nociceptors or increase their sensitivity at the injured site (primary hyperalgesia). Substance P, released by an axon reflex, induces vasodilation and mast cell degranulation, resulting in the release of histamine and serotonin which aid in pro-inflammatory reactions, which in turn sensitize adjacent A-delta and C nociceptors further causing pain stimulation. Increased transduction produces continuous nociceptive input that can induce allodynia, primary hyperalgesia, and secondary hyperalgesia. Ibid., p. 2.

Also within the central nervous system are endogenous pain control systems, which descend the spinal cord through the dorsolateral funiculus to the spinal dorsal horn where they inhibit neurons that are activated by binociceptive stimuli. The higher brain centers connected to these descending systems include the pariaqueductal gray region and various subregions of the medulla within the brain. The neurotransmitters for these systems include substance P, somatostatin, vasoactive intestinal polypeptide, cholecystokinin, calcitonin gene-related peptide, norepinephrine, serotonin and opioid peptides. Ibid., pp. 383–84.

The spinal cord itself also contains opioid receptors, which are mainly localized within laminae-I to III of the dorsal horn within the tract of Lissauer. Of these, the highest density of opioid receptors is generally localized in the inner segment of lamina II. Ibid., p. 384. There are multiple types of opioid receptors within the central nervous system designated as mu, kappa, sigma, and delta receptors, with additional subclasses for each of these receptor types. Activation of these receptors in the brain is believed to be responsible with production of analgesic effects. For example, it is believed that kappa receptors, which exist in the brain's spinal cord, produce analgesia at the spinal level.

The majority of the psychotomimetic effects of opioid drugs, i.e. dysphoria and hallucinations are believed to be mediated by sigma receptors. Delta receptors have a different distribution in the brain, and are thought to be the primary receptor for endogenous opioid pentapeptides, such as enkephalins. Ibid., p. 385.

These types of receptors are located on the membranes of neurons and interaction of agonists, such as narcotic analgesics, with these receptors generally leads to a reduction in excitability and firing rate within the neuron causing a decrease in pain sensation. Agonists of mu receptors, for example, increase the outward flux of potassium ions, which may make the neuron less excitable, causing a decrease in pain. Agonists of kappa receptors more directly inhibit the entry of calcium into a neuron through voltage-dependent calcium channels, again causing a decrease in pain in this manner. Agonists of mu and delta receptors are believed to decrease neuronal cAMP synthesis to decrease pain sensation. Ibid., p. 387.

Thus, the use of opioids, NSAIDS, and many other analgesics within the prior art reduce both central and peripheral sensitization through interaction with the various pain-based receptors within the human body. For example, morphine and most other opioid analgesics elicit an inhibitory neuronal effect within central nervous and gastrointestinal (GI) systems within the human body by interacting with areas of the brain receiving input from the spinal pain-transmitting pathways containing opioid receptors. By suppressing neuronal activity at these receptor points, opioid narcotics produce analgesia and control the pain threshold within a human patient. Yet, opioid narcotics are not without certain negative side effects.

Because opioids cause neuronal depression, frequent side effects which limit the use of such agents in pain treatment settings include drowsiness, lethargy, difficulty in being mobile, respiratory depression, excessive central nervous system depression, weakness in the extremities, and dizziness. Frequently, a patient's respiratory or central nervous system depression by an opioid analgesic will limit the opioid's use or cause its discontinuance from that patient's pain treatment program. This causes prolonged treatment, or use of other agents which may not be as clinically and therapeutically effective.

In addition, patients being treated with opioids also develop tolerance to the agent, requiring higher doses, addition of other opioids to the pain treatment regimen, and the ability to develop physical and psychological addiction to such agents. Further, the prior art has shown that opioids also can exhibit excitatory effects upon opioid receptors. Yet, these excitatory effects manifest themselves as side effects which include restlessness, delirium, mania, and strychnine-like seizure reactions. Such excitatory effects do not occur in all subjects treated with an opioid analgesic, but do appear more prevalently when a patient is treated with morphine or a morphine-like agent. Wingard et al., *Human Pharmacology: Molecular to Clinical*, Mosby-Year Book, Inc., 1991, p. 390.

Finally, other typical side effects of opioid analgesics include miosis, or constriction of the pupils, nausea, vomiting, prolongation of stomach emptying time, decreased propulsive contractions of the small intestine, and increased tone large intestine to slow transit materials through the GI tract. Ibid., pp. 390–91. As a result, most opioid analgesics are only utilized to treat moderate to severe pain, and are used on a short-term basis, only because of these side effects. Ibid., pp. 391–92.

As an alternative to opioid analgesics, non-narcotic based drugs may be utilized to treat mild to moderate pain, and generally because of their lower central nervous system and respiratory depressive effects, can be given over longer periods of time than opioid analgesics. Such non-narcotic agents include acetylsalicylic acid (aspirin), centrally acting alpha antiadrenergic agents, diflusinal, salsalate, acetaminophen, and nonsteroidal anti-inflammatory agents such as ibuprofen, naproxen, and fenoprofen. Ibid., p. 400.

The mechanism by which acetylsalicylic acid, acetaminophen, diflusinal, salsalate, and nonsteroidal anti-inflammatory agents act to reduce mild to moderate pain is through prostaglandin synthesis inhibition resulting in a decrease in pain receptor stimulation. Prior art studies in humans have shown that certain prostaglandins elicit headaches, pain, and can produce hyperalgesia within the central and peripheral neuronal zones of the human body. Aspirin and related compounds inhibit the enzyme cyclooxygenase and prevent the formation of prostaglandin endoperoxides, PGG and PGH, normally formed from arachidonic acid, to reduce or prevent central and peripheral nerve sensitization and nerve stimulation from internal pain agonists. Ibid., p. 400–401.

However, even prostaglandin synthesis inhibitor agents have shown difficulties within the prior art. Aspirin, for example, has been shown through epidemiological data to be a factor in the occurrence of Reye's syndrome. In addition, salicylates in general have been shown within the prior art to cause gastrointestinal upset, gastrointestinal hemorrhage, and anti-platelet effects. Ibid., p. 409. Acetominophen, like aspirin, inhibits cyclooxygenase, but has not been associated with Reye's syndrome or the gastrointestinal effects like that of aspirin. Yet, acetaminophen has been shown within the prior art to cause liver damage, kidney damage, and hematological effects such as hemolytic anemia, neutropenia, and leukopenia. Drug Facts and Comparisons, 1999 ed., 1997, p. 1450.

Lastly, non-steroidal anti-inflammatory drugs, such as ibuprofen, many of which are derived from phenylpropionic acids, can also be used to treat mild to moderate pain, and work mainly by inhibiting cyclooxygenase. These agents exhibit analgesic, anti-inflammatory, and antipyretic effects. These agents, too, however, exhibit numerous negative side effects as well, ranging from gastrointestinal distress, gastrointestinal hemorrhage, and kidney damage. Ibid., p. 409–410.

Centrally acting alpha antiadrenergic agents, such as clonidine, have been shown within the prior art to reduce or prevent central and peripheral nerve agitation. Ibid., p. 967–68, 1444–45. Prior art studies have shown that clonidine, for example, can decrease central and peripheral nerve agitation as well as increased blood pressure through adrenergic impulse inhibition. Yet, centrally acting alpha antiadrenergic agents have been shown to exhibit negative side effects such as central nervous and cardiac system depression, dizziness, drowsiness, lethargy, orthostatic hypotension, and weakness in the extremities. Ibid. In addition, when a centrally acting alpha antiadrenergic agent is added to an already existing pain treatment regimen containing an anxiolytic agent, like lorazepam, an additive effect for dizziness, drowsiness, central and cardiac depression, lethargy, weakness in the extremities, orthostatic hypotension, and difficulty in being mobile occurs. Ibid.

Anxiolytic agents such as benzodiazepines and azaspirodecanediones, although not indicated for the treatment of pain per se, are often employed in pain treatment regimens to decrease the anxiety associated with pain treatment and anxiety associated with further pain stimulus. Yet, the use of anxyiolytic agents in such a pain treatment setting also has the problem of frequent negative side effects.

Clinical neurology literature includes many descriptions of patients having increased drowsiness, dizziness, depression, weakness in the extremities, lethargy, orthostatic hypotension, and difficulty in being mobile associated with treatments utilizing anxiolytic agents and centrally acting alpha antiadrenergic agents for the reduction or prevention of alcohol or narcotic withdrawal symptoms such as anxiety, central and peripheral nerve agitation, and hypertension associated with acute and chronic pain treatment. Dunagan, W. and Ridner, M., *Manual of Medical Therapeutics,* 26th ed., Boston, Little, Brown, 1989, p. 6–7, 474–75.

Clinical cardiology literature in the prior art includes many descriptions of patients experiencing orthostatic hypotension and other side effects associated with centrally acting alpha antiadrenergic agents utilized to treat hypertension and central and peripheral nerve agitation experienced during alcohol or narcotic withdrawal management. Woodley, M. and Whalen A., *Manual of Medical Therapeutics,* 27th ed., Boston, Little, Brown, 1992, p. 64–75.

U.S. Pat. No. 5,668,117 to Shapiro, discloses a method of treating neurological diseases and etiology by utilizing carbonyl-trapping agents in combination with previously known medicaments. Shapiro discloses the ability of combining a carbonyl-trapping agent with either a benzodiazepine or a centrally acting alpha antiadrenergic agent.

U.S. Pat. No. 4,829,070 to Boder, discloses the use of a redox carrier system for the site-specific delivery of a centrally acting therapeutic agent to the brain. Boder discloses the ability of attaching a centrally acting alpha antiadrenergic agent or benzodiazepine to the redox carrier system and delivering those agents to the brain.

U.S. Pat. No. 5,855,908 to Stanley, discloses a non-dissolvable dosage form for use in the transdermal delivery of a drug to a patient, which includes clonidine or a benzodiazepine agent, such as lorazepam, as suitable drugs to be carried by the transdermal system.

Despite the sophistication of new analgesic agents and improved understanding of the neurobiological basis of pain, current pain management treatment modalities involving narcotic, non-narcotic, and anxiolytic therapeutic agents have not been able to manage the side effect issues associated with the use of these agents.

In addition, as the dizziness, drowsiness, depression, lethargy, difficulty in being mobile, weakness in the extremities, orthostatic hypotension, respiratory depression, gastrointestinal distress, and renal distress side effects of these agents occur, therapeutic regimens frequently discontinue one agent for a less successful pain control agent. Patients experiencing side effects become mal- or non-compliant in taking the prescribed pain treatment regimen to manage their particular type of pain. Finally, because of the depressive effects of these agents, healthcare personnel treat patient populations of this type more on an in-patient only setting to minimize liability issues and to monitor abuse potentials by such patients taking these particular medications.

Thus, there is a need within the prior art for a pharmaceutical kit, composition, and a method of treatment regimen which reduces or prevents negative side effect outcomes associated with acute or chronic pain treatment modalities without minimization of mild to severe pain control in a variety of patient populations, ranging from the infant to the elderly adult.

SUMMARY OF THE INVENTION

A pharmaceutical kit, composition and method of treatment regimen for the management of side effects associated with therapeutic agents used to treat acute and chronic pain syndromes has been discovered, utilizing a centrally acting alpha antiadrenergic agent, central nervous system stimulant agent, and an anxiolytic agent combination. The present invention reduces or prevents the negative side effects of depression, dizziness, drowsiness, lethargy, weakness in the extremities, difficulty in being mobile, orthostatic hypotension, restlessness, delirium and mania associated with therapeutic agents utilized to treat acute and chronic pain syndromes without compromising positive clinical effects of those same therapeutic agents.

By reducing or preventing these side effects, the present invention also decreases the risk of injury to patients and liability to healthcare personnel treating such patient populations. Further, by reducing the risk, such pain treatment patients have an increased opportunity to be treated in an outpatient setting, which in turn decreases the healthcare cost in treating these individuals. Further, by minimizing side effects to patients undergoing pain syndrome treatment with the present invention, incidences of therapeutic agent addiction psychologically or physically are reduced or prevented.

The present invention can be embodied in a variety of pharmaceutically acceptable immediate and sustained release dosage forms and can be delivered to the human body via a variety of medically and pharmaceutically acceptable administration routes.

These and other features, advantages and objects of the present invention will be further understood and appreciated by those skilled in the art by reference to the following specification, claims and appended drawings. A more detailed description of the present invention shall be discussed further below.

DETAILED DESCRIPTION OF THE PRESENT INVENTION

Figure 1:
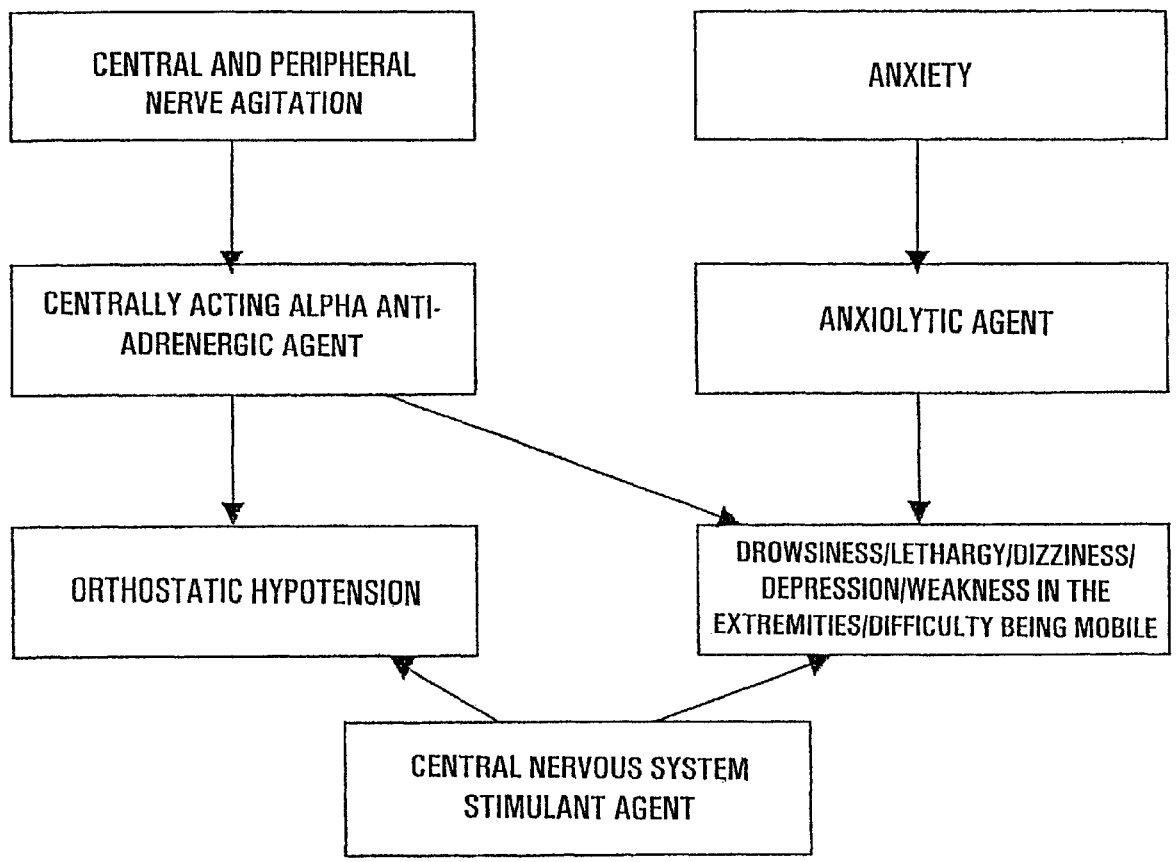
FIG. 1 is a flow diagram indicating the prevention or reduction of side effects associated with therapeutic agents used to treat acute and chronic pain syndromes, through the use of the triple drug combination of the preferred embodiment, without compromising the positive clinical effects of those same therapeutic agents.

The preferred embodiment comprises of a pharmaceutical kit, composition, method of treatment regimen containing a combination of effective amounts of an anxiolytic agent, centrally acting alpha antiadrenergic agent, and central nervous system (CNS) stimulant agent for the reduction or prevention of the negative side effects of drowsiness, dizziness, depression, weakness in the extremities, lethargy, orthostatic hypotension, restlessness, delirium, mania, and difficulty in being mobile associated with therapeutic agents utilized to treat acute and chronic pain syndromes.

The anxiolytic agent utilized in the present invention consists of an effective amount of a benzodiazepine, azaspirodecanedione, piperazine derivative or gabapentin. Suitable benzodiazepine agents include, but are not limited to, diazepam, alprazolam, clonazepam, chlordiazepoxide, clorazepate, halazepam, lorazepam, oxazepam, derivatives thereof, and pharmaceutically acceptable salts thereof. Suitable azaspirodecanedione agents include, but are not limited to, buspirone, derivatives thereof, and pharmaceutically acceptable salts thereof. Suitable piperazine derivatives include, but are not limited to, hydroxyzine prorate and hydroxyzine hydrochloride, derivatives thereof, and pharmaceutically acceptable salts thereof.

Gabapentin is not known as an anxiolytic agent, per se. It does, however, have anxiolytic properties, and hence for purposes of this patent application it is included within the scope of the term "anxiolytic agent" as used herein.

Gabapentin has been approved for "add-on" treatment of partial epileptic seizures. This interesting drug is an analog of the inhibitory neurotransmitter gamma-aminobutyric acid (GABA) and was initially thought to act via GABAergic mechanisms. However, researchers found that gabapentin does not interact with GABA receptors, nor does it interfere with GABA metabolism. There is some evidence that gabapentin may increase the GABA content of some brain regions, but the significance of this finding is not known. Unlike phenytoin or carbamazepine, gabapentin does not interact with sodium channels, nor does it influence receptors for benzodiazepeines, opioids, catecholamines, or acetylcholine. Instead, gabapentin appears to act by binding a specific protein found only on neurons in the central nervous system. This protein, which does not appear to bind any other antiepileptic drug, is found in highest density in areas of the neocortex that are rich in synapses containing the excitatory neurotransmitter glutamine. Pharmaceutical Information Associates, Ltd., *Medical Sciences Bulletin*, p. 1, February 1994. It should be used in amounts of from about 300 mg to about 4000 mg per day.

Although not wanting to be bound to any particular theory, glutamate excitotoxicity, as discussed within clinical gabapentin literature, plays an important role in neuronal excitability, production of a nociceptive stimulus, and negative affective outcome in human pain syndromes. *The Natural History and the Effects of Gabapentin in Amytrophic Lateral Sclerosis*, Journal of Neurological Science, 1998October; 160; Supp. 1: S57–63. In vitro, gabapentin has been shown to modulate the action of gamma-aminobutyric acid (GABA) synthetic enzyme, glutamic acid decarboxylase (GAD) and the glutamate synthesizing enzyme, branched-chain amino acid transaminase. *Mechanisms of Action of Gabapentin*, Review Neurology (Paris), 1997; 153 Supp. 1: S39–45. Such actions indicate that gabapentin increases GABA synthesis and thus enhances the resultant anxiolytic effect of GABA, which is beneficial in pain control.

Further, gabapentin has demonstrated, in vitro, inhibitory effects on voltage-gated ion channels (sodium, calcium). *Gabapentin*, Neuropsychobiology, 1998October; 38(3); 139–44. In particular, it has recently been suggested that gabapentin interacts with a high-affinity binding site in brain membranes known as an auxiliary subunit of voltage sensitive calcium channels. Again, although not wanting to be bound to any particular theory, it is believed that the recently identified alpha2delta subunit (predominantly the L-type) of a voltage-gated calcium channel acts as a high affinity binding site for gabapentin. *Gabapentin Inhibits Calcium Currents in Isolated Rat Brain Neurons*. Neuropharmacology, 1998; 37(1): 83–91. In doing so, gabapentin binds to such a site to inhibit intracellular calcium accumulation within neurons to decrease their resultant level of excitability. Id. By decreasing neuronal excitability, gabapentin has the capability to decrease pain sensation and to exhibit an anxiolytic type effect.

The preferred anxiolytic agent for the management of acute or chronic pain syndromes is about 50–60 mg of chlordiazepoxide given to a human being every 6–8 hours around the clock initially, and gradually tapered by about 10 mg per day for a period of about 5–14 days. While not wanting to be bound by any particular theory, it is believed that the anxiolytic agent of the preferred embodiment reduces or prevents the anxiety, restlessness, delirium, and mania side effects of therapeutic agents used to treat mild to severe pain associated with acute and chronic pain syndromes. In doing so, the anxiolytic agent decreases central and peripheral nerve sensitization to painful stimuli by managing these negative side effects without deleterious effect upon the positive pain control effects of the conventional therapeutic agents used to the mild to severe pain associated with the acute or chronic pain syndrome.

As an alternative to the chlordizepoxide being the anxiolytic agent within the preferred embodiment, about 0.25–10 mg of lorazepam given to a human being about every 4–10 hours, preferably about every 6–10 hours, and most preferably about every 6–8 hours during the day and about every 3–4 hours at night up to a typical maximum dose of about 10 mg or greater, most preferably a maximum of about 7 mg a day or greater can be utilized instead. Total daily dosing will occur over about 5–14 days, with initial doses maximizing at about 7–10 mg a day and tapering thereafter by about 1 mg or greater each day of treatment until dosing is completed within a period of about 5–14 days.

Those skilled in the art will appreciate and be able to adjust the dose, dosing interval, and dosing length/treatment period of the anxiolytic agent of the preferred embodiment in the treatment of acute or chronic pain syndromes, based upon the clinical response and therapeutic value required to reduce or prevent the negative side effect outcomes associated with therapeutic agents used to treat such syndromes. One skilled in the art will be able to appreciate and adjust the dose, dosing interval, and length of treatment with the anxiolytic agent of the preferred embodiment based upon the liver and kidney function of the patient and the amount of CNS stimulant agent used as part of the preferred embodiment.

For example, as the dose of the CNS stimulant of the preferred embodiment is increased or the interval dosing is decreased, the anxiolytic agent dose can be decreased and dosing interval increased. In addition, it should be understood by those skilled in the art that the dose of the CNS stimulant can be used to achieve therapeutic efficacy in managing the negative side outcomes of the anxiolytic agent, itself, within the preferred embodiment as the dose of the anxiolytic agent is increased to treat anxiety, restlessness, delirium, and mania associated with the therapeutic agents used to treat acute and chronic pain syndromes.

The centrally acting alpha antiadrenergic agent of the preferred embodiment consists of an effective amount of methyldopa, clonidine, guanfacine, guanabenz, lofexidine, derivatives thereof or pharmaceutically acceptable salts thereof. It is recognized that lofexidine is not currently approved for use in the U.S. by the FDA but is approved for use in Europe. The preferred centrally acting alpha antiadrenergic agent for the treatment of acute and chronic pain syndromes is about 0.05–0.7 mg clonidine given to a human being for a period of 6–8 hours for about 5–14 days.

Although not wanting to be bound by any particular theory, it is believed that the use of such agents reduces or prevents central and peripheral nerve agitation associated with acute and chronic pain syndromes while minimizing the negative side effects of restlessness, delirium, and mania cause by other narcotic or non-narcotic agents, which may be added to a particular pain treatment regimen. Typical maximal dosages of clonidine can be about 2 mg per day or higher depending upon the patient response required for the acute or chronic pain setting, liver and kidney function of the patient, and the dose and dosing interval of the central nervous system stimulant agent of the preferred embodiment during that patient's pain treatment course.

As the dose of the CNS stimulant is increased, or the dosing interval is decreased, the centrally acting alpha antiadrenergic agent dose can be decreased and dosing interval increased. In addition, it should be understood by those skilled in the art that the dose of the CNS stimulant can be increased to achieve therapeutic efficacy while managing the negative side effect outcomes of the centrally acting alpha antiadrenergic and anxiolytic agents of the preferred embodiment as the dose of those agents are increased to treat acute and chronic pain syndromes.

The central nervous system stimulant agent of the preferred embodiment consists of an effective amount of an amphetamine, such as an amphetamine sulfate, dextroamphetamine sulfate, methylamphetamine hydrochloride, combinations of such amphetamines, derivatives thereof and pharmaceutically acceptable salts thereof; pemoline, derivatives thereof and pharmaceutically acceptable salts thereof; methylphenidate, derivatives and pharmaceutically acceptable salts thereof; caffeine, derivatives and pharmaceutically acceptable salts thereof; and centrally acting alpha-1 agonists such as modafinil, norepinephrine, phenylephrine, and derivatives and pharmaceutically acceptable salts thereof.

While again not wanting to be bound to any particular theory, it is believed that the central nervous system stimulant agent of the preferred embodiment acts to reduce or prevent dizziness, depression, difficulty in being mobile, drowsiness, lethargy, weakness in the extremities, and orthostatic hypotension associated with therapeutic agents utilized to treat acute and chronic pain syndromes such as the anxiolytic and centrally acting alpha antiadrenergic agent components of the preferred embodiment without detracting from the positive clinical effects provided by those particular agents in treating acute and chronic pain syndromes.

It is believed that the central nervous system stimulant agent releases increased norepinephrine from central nonadrenergic neurons, epinephrine from adrenergic neurons, and dopamine from the human central nervous system to counteract the negative side effects of central nervous system depressants such as narcotic, non-narcotic, centrally acting alpha antiadrenergic, and anxiolytic agents used to treat acute and chronic pain syndromes.

The preferred central nervous system stimulant agent of the preferred embodiment consists of from about 1–20 mg of dextroamphetamine sulfate in an immediate release dosage form given to a human being about every 4–8 hours, preferably every 4–6 hours at a regular spaced interval during the day and up to about 5 mg as a rescue dose during the night if needed for a period of about 5–14 days. In a controlled release dosage form, the central nervous system stimulant, dextroamphetamine sulfate, is dosed as 1–20 mg given to a human being about every 12 hours or once daily without a rescue dose given during the night, for a total treatment period/dosing length of about 5–14 days.

In an alternative embodiment, for those patients requiring a non-amphetamine based central nervous system stimulant agent or those patients who cannot receive additional or increased amphetamine doses due to cardiovascular risk concerns, a centrally acting alpha-1 agonist such as modafinil, can be used as a substitute or in addition to the amphetamine(s) component of the central nervous system stimulant agent of the preferred embodiment.

Centrally acting alpha-1 agonists such as modafinil (Provigil®) act postsynaptically at alpha-1 adrenergic receptors and may also bind to dopamine carriers to increase stimulation and mental alertness within the human body, usually without altering the body's blood pressure or heart rate excessively, like that of amphetamines. Further, centrally acting alpha-1 agonists do not decrease stage 2 REM sleep like amphetamines, and thus offer a treatment alternative for the practitioner when choosing a central nervous system stimulant agent of the preferred embodiment.

In the alternative embodiment, the preferred central nervous system stimulant agent is about 50–400 mg, preferably about 100–300 mg, and most preferably about 200 mg or higher per day of modafinil given to a human being administered every 12 hours, preferably once daily in the morning for a period of 5–14 days.

It should be understood by those skilled in the art that the preferred embodiment of the present invention can utilize any of the central nervous stimulant agents alone or in combination with one another as the central nervous system stimulant agent component of the preferred embodiment. For example, a practitioner administering the preferred embodiment containing an amphetamine initially as a central nervous system stimulant agent could add modafinil as an adjunct central nervous system stimulant to a patient's treatment therapy, where use of an additional amount of the original amphetamine would not be desirable, due to therapeutic and adverse effect outcome considerations. Thus, modafinil would allow a practitioner to increase central nervous system stimulation without increasing the negative cardiovascular side effects of the amphetamine agent.

Those skilled in the art would be able to adjust the dose, dosing interval and dosing length/treatment period of the central nervous system stimulant of the present invention based upon the clinical and therapeutic response desired for a patient undergoing acute and chronic pain syndrome treatment, liver and kidney function of that patient, as well as drug interaction potential between this agent and other components of the preferred embodiment.

All of the components of the preferred embodiment can be used separately, but administered contemporaneously, and can be given via a singular pharmaceutically acceptable dosage form for each component or combination of all the components as an immediate release or controlled release dosage form. Contemporaneously means the three agents are administered separately over time, but have a combined effect together after their individual administrations. Suitable pharmaceutical dosage forms for the preferred embodiment include, but are not limited to, tablets, capsules, caplets, dose-paks, solutions, syrups, suppositories, transdermal applications, creams, lotions, emulsions, powders and the like. Preferred dosage forms for the present invention include tablets, caplets, capsules, dose-paks, solutions, and transdermal applications with a tablet, capsule, or caplet being the most preferred.

The triple drug therapeutic composition, kit, and method of treatment of the preferred embodiment can be administered to the human body via a variety of medically and pharmaceutically acceptable administration routes. Those routes include, but are not limited to the oral, rectal, intravenous, intradermal, subcutaneous, cutaneous, intramuscular, buccal, transdermal, and other pharmaceutically and medically acceptable routes of administration for the human body. Preferred routes of administration for the preferred embodiment are the oral, rectal, intravenous and intramuscular routes, with the oral route being most preferred.

By combining the pharmaceutical medicaments of the preferred embodiment in a new and novel kit, composition, and method of treatment regimen, the preferred embodiment achieves far superior negative side effect management results for therapeutic agents utilized to treat acute and chronic pain syndromes resulting in enhanced reduction or prevention of acute and chronic mild to severe pain. Further, the preferred embodiment reduces the risk to patients as well as treating healthcare personnel to allow for more outpatient treatment settings, which reduces the overall cost of healthcare. Lastly, the preferred embodiment also decreases side effect considerations for the anxiolytic and centrally acting antiadrenergic agents of the preferred embodiment increasing their acceptability, use, and positive pain reduction capabilities in treating acute or chronic mild to severe pain syndromes.

The following observational examples illustrate the clinical outcomes associated with use of the triple drug combination of the preferred embodiment in treating various forms of acute or chronic pain.

EXAMPLE ONE

Chronic Spinal Nerve Pain Treatment

A 37-year-old patient suffered a spinal nerve injury after a car accident. Six years after the accident, the patient still suffered from chronic back pain emanating from the point of injury throughout the entire back. Symptoms of the neuropathy included radiating pain down the legs and inflammation at the injury site. Due to the back pain and a treatment period for kidney stones, the patient received multiple doses of the prescription drug Vicodan.

Following kidney stone treatment and back pain management, the patient began increased use of Vicodan to a point of ingesting 15 to 20 pills per day, finally requiring narcotic abuse treatment. While undergoing detoxification for addiction to Vicodan, the patient received the following medication protocol:

Day 1: 0.4 mg clonidine, 2 mg lorazepam, and 5 mg dexedrine

Day 2: 0.6 mg clonidine, 3 mg lorazepam, and 5 mg dexedrine

Day 3: 0.8 mg clonidine, 4 mg lorazepam, and 5 mg dexedrine

Day 4: 0.6 mg clonidine, 3 mg lorazepam, and 5 mg dexedrine

Day 5: 0.3 mg clonidine, 1.5 mg lorazepam, and 2.5 mg dexedrine

Day 6: 0.3 mg clonidine, 1.5 mg lorazepam, and 2.5 mg dexedrine

Day 7: 0.2 mg clonidine, 1 mg lorazepam, and 2.5 mg dexedrine

During the detoxification procedure, subjective and objective clinical assessment was completed at which time the patient indicated a significant reduction in chronic back pain while receiving the treatment regimen. Following the detoxification procedure, the patient reported less pain than prior to the procedure, yet, experienced increased pain once the triple drug treatment regimen was discontinued. However, as a consequence of pain rebound following withdrawal treatment, the patient was continued on the medication protocol at very low doses, during which time the patient again continued to experience a reduction in chronic back pain. The results of the case report illustrate the ability of the triple drug regimen of the preferred embodiment's ability to significantly alleviate chronic forms of pain.

EXAMPLE 2

Tooth Pain

A 32-year-old female patient presented at the time of narcotic abuse treatment with a history of significant, recurring, but not chronic tooth pain. The patient required narcotic abuse treatment following use of the prescription drug Percodan for approximately three months to treat the tooth pain. However, the patient experienced severe withdrawal symptoms during each discontinuance of the narcotic analgesic. To treat the withdrawal symptomology, the patient was given the following low-dose detoxification treatment regimen:

Day 1: 0.3 mg clonidine, 1.5 mg lorazepam, and 2.5 mg dexedrine

Day 2: 2.5 mg clonidine, 0.5 mg lorazepam, and 2.5 mg dexedrine

Day 3: 0.3 mg clonidine, 1.5 mg lorazepam, and 2.5 mg dexedrine

Day 4: 0.2 mg clonidine, 1 mg lorazepam, and 0 mg dexedrine

Day 5: 0.2 mg clonidine, 1 mg lorazepam, and 0 mg dexedrine

During the detoxification treatment program, the patient was able to discontinue the use of Percodan without recurrent painful tooth episodes. The patient reported significant reduction in tooth pain and did not experience a rebound in tooth pain following discontinuance of the opioid as would have been expected. Following the triple drug treatment program, the patient reported increased tooth pain. The results of the observational case study indicate the ability of the triple drug regimen of the preferred embodiment to decrease acute forms of pain such as tooth pain.

EXAMPLE 3

Surgical Pain

A 41-year-old female patient had undergone corrective knee surgery. Following the surgical procedure, the patient received the prescription drug, Tylenol #4, to treat pain related to the surgical procedure. Having the pain unrelieved by Tylenol #4 over a period of eight weeks, the patient began to use heroin to relieve the pain and quickly became addicted to the agent. The patient was treated for withdrawal symptomology with the following protocol:

Day 1: 0.6 mg clonidine, 3 mg lorazepam, and 5 mg dexedrine

Day 2: 0.8 mg clonidine, 4 mg lorazepam, and 5 mg dexedrine

Day 3: 0.8 mg clonidine, 4 mg lorazepam, and 5 mg dexedrine

Day 4: 0.6 mg clonidine, 3 mg lorazepam, and 5 mg dexedrine

Day 5: 0.6 mg clonidine, 3 mg lorazepam, and 5 mg dexedrine

Day 6: 0.3 mg clonidine, 1.5 mg lorazepam, and 5 mg dexedrine

Day 7: 0.2 mg clonidine, 1 mg lorazepam, and 2.5 mg dexedrine

By the second day of detoxification treatment, the patient reported a significant reduction in knee pain. By the end of the week of treatment, the patient reported that the knee pain had been substantially abated. As can be seen by this observational case study, traumatic pain such as that induced by surgical procedure can be substantially reduced or prevented by the triple drug regimen of the preferred embodiment.

EXAMPLE 4

Pain Associated with Alcohol and Narcotic Withdrawal

A 29-year-old patient underwent alcohol and narcotic abuse treatment following an episode of withdrawal symptomology in which the patient experienced the withdrawal side effects of dysphoria, anxiety, nausea, vomiting, abdominal cramping, tremors, fever, pupil dilation, and sweating. The patient was treated with a detoxification regimen to manage the withdrawal symptomology caused by the patient's daily ingestion of five "bags" of heroin and two quarts of vodka over a period of two years. The detoxification regimen was as follows:

Day 1: 0.8 mg clonidine, 4 mg lorazepam, and 5 mg dexedrine

Day 2: 0.8 mg clonidine, 4 mg lorazepam, and 5 mg dexedrine

Day 3: 0.4 mg clonidine, 2 mg lorazepam, and 5 mg dexedrine

Day 4: 0.3 mg clonidine, 1.5 mg lorazepam, and 5 mg dexedrine

Following Day One's course of therapy, the patient reported a significant withdrawal symptomology such as anxiety, dysphoria, abdominal cramping, sweating, and tremor. As the patient's treatment regimen continued beyond Day Four with reductions in each of the three medications listed, the patient still noted few withdrawal symptoms and eventually was weaned from the alcohol and narcotic usage.

It should be noted that in each of Examples 1–4, the patient's were treated initially in an inpatient setting, and then were moved to an outpatient setting, which could not have been done previously utilizing pain treatment methods within the prior art. By allowing the patients to be treated in an outpatient setting, the patients became more compliant in the drug therapy, achieved greater rates of return to normal daily activities, and had a significantly reduced cost of healthcare during their course of treatment.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the Doctrine of Equivalents.

The invention claimed is:

1. A pharmaceutical kit for the treatment of acute and chronic pain syndrome comprising the combination of:
   at least one anxiolytic agent;
   at least one centrally acting alpha antiadrenergic agent; and
   at least one central nervous system stimulant agent.

2. The pharmaceutical kit of claim 1, wherein said kit contains an effective amount of said anxiolytic agent to reduce or prevent anxiety, an effective amount of said centrally acting alpha antiadrenergic agent to reduce or prevent central and peripheral nerve agitation, and an effective amount of said central nervous system stimulant agent to reduce or prevent negative side effects associated with acute and chronic pain syndrome treatment.

3. The pharmaceutical kit of claim 2, wherein said anxiolytic agent comprises at least one member selected from the group consisting of a benzodiazepine, azaspirodecanedione, hydroxyzine pamoate, hydroxyzine hydrochloride, gabapentin, and pharmaceutically acceptable salts thereof.

4. The pharmaceutical kit of claim 3, wherein said anxiolytic agent is a benzodiazepine selected from the group consisting of diazepam, alprazolam, clonazepam, clorazepate, chlordiazepoxide, halazepam, lorazepam, oxazepam, and pharmaceutically acceptable salts thereof.

5. The pharmaceutical kit of claim 4, wherein said benzodiazepine is chlordiazepoxide.

6. The pharmaceutical kit of claim 5, wherein said effective amount of said chlordiazepoxide is about 50–60 mg per dose.

7. The pharmaceutical kit of claim 3, wherein said benzodiazepine is lorazepam and said effective amount of said lorazepam is about 0.25–10 mg per dose.

8. The pharmaceutical kit of claim 2, wherein said anxiolytic agent is gabapentin and said effective amount of said gabapentin is from about 300 mg to 4000 mg per day.

9. The pharmaceutical kit of claim 2, wherein said centrally acting alpha antiadrenergic agent comprises of at least one member selected from the group consisting of methyldopa, clonidine, guanfacine, lofexidine, guanabenz, and pharmaceutically acceptable salts thereof.

10. The pharmaceutical kit of claim 9, wherein said centrally acting alpha antiadrenergic agent is clonidine and said effective amount of said clonidine is about 0.05–0.7 mg per dose.

11. The pharmaceutical kit of claim 2, wherein said central nervous system stimulant agent comprises of at least one member selected from the group consisting of an amphetamine, methylphenidate, pemoline, caffeine, a centrally acting alpha-1 agonist, and pharmaceutically acceptable salts thereof.

12. The pharmaceutical kit of claim 11, wherein said central nervous system stimulant is an amphetamine, said amphetamine is dextroamphetamine sulfate and said effective amount of said dextroamphetamine sulfate is about 1–20 mg per dose.

13. The pharmaceutical kit of claim 12, wherein said dextroamphetamine sulfate is in a sustained release form.

14. The pharmaceutical kit of claim 11, wherein said central nervous system stimulant agent is a centrally acting alpha-1 agonist, said centrally acting alpha-1 agonist is modafinil and said effective amount of said modafinil is about 50–400 mg or greater per dose.

15. The pharmaceutical kit of claim 14, wherein said effective amount of said modafinil is about 200 mg per dose.

16. The pharmaceutical kit of claim 2, wherein said anxiolytic agent comprises at least one member selected from the group consisting of a benzodiazepine, azaspirodecanedione, hydroxyzine pamoate, hydroxyzine hydrochloride, gabapentin, and pharmaceutically acceptable salts thereof; wherein said centrally acting alpha antiadrenergic agent comprises at least one member selected from the group consisting of methyl dopa, clonidine, guanfacine, lofexidine, guanabenz, and pharmaceutically acceptable salts thereof; wherein said central nervous system stimulant agent comprises of at least one member selected from the group consisting of an amphetamine, methylphenidate, pemoline, caffeine, centrally acting alpha-1 agonist, and pharmaceutically acceptable salts thereof.

17. The pharmaceutical kit of claim 1, wherein said at least one anxiolytic agent comprises about 0.25–10 mg of lorazepam, said at least one centrally acting alpha antiadrenergic agent comprises about 0.05–7 mg of clonidine, and said at least one central nervous system stimulant agent comprises about 1–20 mg of dextroamphetamine sulfate per dose of said combination.

18. The pharmaceutical kit of claim 1, wherein said at least one anxiolytic agent comprises about 50–60 mg of chlordiazepoxide, said at least one centrally acting alpha antiadrenergic agent comprises about 0.05–0.7 mg of clonidine, and said at least one central nervous system stimulant agent comprises about 1–20 mg of dextroamphetamine sulfate per dose of said combination.

19. The pharmaceutical kit of claim 1, wherein said at least one anxiolytic agent comprises about 0.25–10 mg of lorazepam, said at least one centrally acting alpha antiadrenergic agent comprises about 0.05–0.7 mg of clonidine, and said at least one central nervous system stimulant agent comprises about 50–400 mg of modafinil per dose of said combination.

20. The pharmaceutical kit of claim 1, wherein said at least one anxiolytic agent comprises about 50–60 mg of chlordiazepoxide, said at least one centrally acting alpha antiadrenergic agent comprises about 0.05–0.7 mg of clonidine, and said at least one central nervous system stimulant agent comprises about 50–400 mg of modafinil per dose of said combination.

21. The pharmaceutical kit of claim 1, wherein said at least one anxiolytic agent comprises about 0.25–10 mg of lorazepam, said at least one centrally acting alpha antiadrenergic agent comprises about 0.05–0.7 mg of clonidine, and said at least one central nervous system stimulant agent comprises about 50–400 mg of modafinil, and about 1–20 mg of dextroamphetamine sulfate per dose of said combination.

22. The pharmaceutical kit of claim 1, wherein said at least one anxiolytic agent comprises about 50–60 mg of chlordiazepoxide, said at least one centrally acting alpha antiadrenergic agent comprises about 0.05–0.7 mg of clonidine, and said at least one central nervous system stimulant agent comprises about 1–20 mg of dextroamphetamine sulfate, and about 50–400 mg of modafinil per dose of said combination.

23. A pharmaceutical composition for the treatment of acute and chronic pain syndrome comprising a combination of at least one anxiolytic agent; at least one centrally acting alpha antiadrenergic agent; and at least one central nervous system stimulant agent.

24. The pharmaceutical composition of claim 23, wherein said composition comprises of an effective amount of said anxiolytic agent to reduce or prevent anxiety, an effective amount of said centrally acting alpha antiadrenergic agent to reduce or prevent central and peripheral nerve agitation, and an effective amount of said central nervous system stimulant agent to reduce or prevent negative side effects associated with acute and chronic pain syndrome treatment.

25. The pharmaceutical composition of claim 24, wherein said anxiolytic agent comprises at least one member selected from the group consisting of a benzodiazepine, azaspirodecanedione, hydroxyzine pamoate, hydroxyzine hydrochloride, gabapentin, or pharmaceutically acceptable salts thereof.

26. The pharmaceutical composition of claim 25, wherein said anxiolytic agent is a benzodiazepine selected from the group consisting of diazepam, alprazolam, clonazepam, clorazepate, chlordiazepoxide, halazepam, lorazepam, oxazepam, or pharmaceutically acceptable salts thereof.

27. The pharmaceutical composition of claim 26, wherein said benzodiazepine is chlordiazepoxide.

28. The pharmaceutical composition of claim 27, wherein said effective amount of said chlordiazepoxide is about 50–60 mg per dose.

29. The pharmaceutical composition of claim 26, wherein said benzodiazepine is lorazepam and said effective amount of said lorazepam is about 0.25–10 mg per dose.

30. The pharmaceutical composition of claim 24, wherein said centrally acting alpha antiadrenergic agent comprises of at least one member selected front the group consisting of methyldopa, clonidine, guanfacine, lofexidine, guanabenz, and pharmaceutically acceptable salts thereof.

31. The pharmaceutical composition of claim 24, wherein said centrally acting alpha antiadrenergic agent comprises of at least one member selected from the group consisting of methyldopa, clonidine, guanfacine, guanabenz, lofexidine, and pharmaceutically acceptable salts thereof.

32. The pharmaceutical composition of claim 31, wherein said centrally acting alpha antiadrenergic agent is clonidine and said effective amount of said clonidine is about 0.05–0.7 mg per dose.

33. The pharmaceutical composition of claim 24, wherein said central nervous system stimulant agent comprises of at least one member selected from the group consisting of an amphetamine, methylphenidate, pemoline, caffeine, centrally acting alpha-1 agonist, and pharmaceutically acceptable salts thereof.

34. The pharmaceutical composition of claim 33, wherein said central nervous system stimulant is an amphetamine, said amphetamine is dextroamphetamine sulfate and said effective amount of said dextroamphetamine sulfate is about 1–20 mg per dose.

35. The pharmaceutical composition of claim 34, wherein said effective amount of said dextroamphetamine sulfate is in a sustained release form.

36. The pharmaceutical composition of claim 33, wherein said central nervous system stimulant agent is a centrally acting alpha-1 agonist, said centrally acting alpha-1 agonist is modafinil and said effective amount of said modafinil is about 50–400 mg per dose.

37. The pharmaceutical composition of claim 36, wherein said effective amount of said modafinil is about 200 mg per dose.

38. The pharmaceutical composition of claim 23, wherein said at least one anxiolytic agent comprises about 0.25–10 mg lorazepam, said at least one centrally acting alpha antiadrenergic agent comprises about 0.05–0.7 mg of clonidine, and said at least one central nervous system stimulant agent comprises about 1–20 mg of dextroamphetamine sulfate per dose of said combination.

39. The pharmaceutical composition of claim 23, wherein said at least one anxiolytic agent comprises about 100 mg or less of chlordiazepoxide, said at least one centrally acting alpha antiadrenergic agent comprises about 0.05–0.7 mg of clonidine, and said at least one central nervous system stimulant agent comprises about 1–20 mg of dextroamphetamine sulfate per dose of said combination.

40. The pharmaceutical composition of claim 23, wherein said at least one anxiolytic agent comprises about 0.25–10 mg of lorazepam, said at least one centrally acting alpha antiadrenergic agent comprises about 0.05–0.7 mg of clonidine, and said at least one central nervous system stimulant agent comprises about 50–400 mg of modafinil per dose of said combination.

41. The pharmaceutical composition of claim 23, wherein said at least one anxiolytic agent comprises about 100 mg or less of chlordiazepoxide, said at least one centrally acting alpha antiadrenergic agent comprises about 0.05–0.7 mg of clonidine, and said at least one central nervous system stimulant agent comprises about 50–400 mg of modafinil per dose of said combination.

42. The pharmaceutical composition of claim 23, wherein said at least one anxiolytic agent comprises about 0.25–10 mg of lorazepam, said at least one centrally acting alpha antiadrenergic agent comprises about 0.05–0.7 mg of clonidine, and said at least one central nervous system stimulant agent comprises about 50–400 mg of modafinil, and about 1–20 mg of dextroamphetamine sulfate per dose of said combination.

43. The pharmaceutical composition of claim 23, wherein said at least one anxiolytic agent comprises about 100 mg or less of chlordiazepoxide, said at least one centrally acting alpha antiadrenergic agent comprises about 0.05–0.7 mg of clonidine, and said at least one central nervous system stimulant agent comprises about 1–20 mg of dextroamphetamine sulfate, and about 50–400 mg modafinil per dose of said combination.

44. A method for treating and preventing acute and chronic pain syndrome, administering separately, but contemporaneously, a combination of at least one anxiolytic agent, at least one centrally acting alpha antiadrenergic agent, and at least one central nervous system stimulant agent.

45. The method of claim 44, wherein said at least one anxiolytic agent is administered in an amount effective to reduce or prevent anxiety, said at least one centrally acting alpha antiadrenergic agent is administered in an amount effective to reduce or prevent central and peripheral nerve agitation, and said at least one central nervous system stimulant agent is administered in an amount effective to reduce or prevent negative side effects associated with acute and chronic pain syndrome treatment.

46. The method of claim 45, wherein said anxiolytic agent comprises at least one member selected from the group consisting of a benzodiazepine, azaspirodecanedione, hydroxyzine pamoate, hydroxyzine hydrochloride, gabapentin, and pharmaceutically acceptable salts thereof, and further wherein said benzodiazepine comprises at least one member selected from the group consisting of diazepam, alprazolam, clonazepam, clorazepate, chlordiazepoxide, halazepam, lorazepam, oxazepam, and pharmaceutically acceptable salts thereof.

47. The method of claim 46, wherein said anxiolytic agent is chlordiazepoxide.

48. The method of claim 47, wherein said effective amount of said chlordiazepoxide is about 50–60 mg administered about every 6–8 hours around the clock initially and gradually tapering said effective amount of said chlordiazepoxide thereafter for a period of about 5–14 days.

49. The method of claim 46, wherein said anxiolytic agent is lorazepam and said effective amount of said lorazepam is about 0.25–10 mg administered about every 6–8 hours during the day and about every 3–4 hours during the night initially, and gradually tapering said effective amount of said lorazepam thereafter for a period of about 5–14 days.

50. The method of claim 45, wherein said centrally acting alpha antiadrenergic agent comprises of at least one member selected from the group consisting of methyldopa, clonidine, guanfacine, lofexidine, guanabenz, and pharmaceutically acceptable salts thereof.

51. The method of claim 46, wherein said centrally acting alpha antiadrenergic agent comprises at least one member selected from the group consisting of methyldopa, clonidine, guanfacine, guanabenz, lofexidine, and pharmaceutically acceptable salts thereof.

52. The method of claim 46, wherein said centrally acting alpha antiadrenergic agent is clonidine and said effective amount of clonidine is about 0.05–7 mg administered about every 6–8 hours for a period of about 5–14 days.

53. The method of claim 46, wherein said central nervous system stimulant comprises at least one member selected from the group consisting of an amphetamine, methylphenidate, pemoline, caffeine, centrally acting alpha-1 agonist, and pharmaceutically acceptable salts thereof.

54. The method of claim 53, wherein said central nervous system stimulant is an amphetamine, said amphetamine is dextroamphetamine sulfate and said effective amount of said dextroamphetamine sulfate is about 1–20 mg administered about every 4–6 hours during the day and up to about 5 mg during the night if needed for a period of about 5–14 days.

55. The method of claim 53, wherein said central nervous system stimulant is an amphetamine, said amphetamine is dextroamphetamine sulfate and said effective amount of dextroamphetamine sulfate is about 1–20 mg in a sustained release form administered about every 12 hours to about once daily for a period of about 5–14 days.

56. The method of claim 45, wherein said anxiolytic agent comprises at least one member selected from the group consisting of a benzodiazepine, azaspirodecanedione, hydroxyzine pamoate, hydroxyzine hydrochloride, gabapentin, and pharmaceutically acceptable salts thereofl; wherein said centrally acting alpha antiadrenergic agent comprises at least one member selected from the group consisting of methyldopa, guanabenz, guanfacine, clonidine, lofexidine, and pharmaceutically acceptable salts thereof, wherein said central nervous system stimulant agent comprises at least one member selected from the group consisting of an amphetamine, methylphenidate, pemoline, caffeine, centrally acting alpha-1 agonist, and pharmaceutically acceptable salts thereof.

57. The method of claim 45, wherein said effective amount of said at least one anxiolytic agent is about 50–60 mg of chlordiazepoxide administered about every 6–8 hours around the clock initially and gradually tapering said chlordiazepoxide thereafter;
   said effective amount of said at least one centrally acting alpha antiadrenergic agent is about 0.05–0.7 mg of clonidine administered about every 6–8 hours; and
   said effective amount of said at least one central nervous system stimulant is about 1–20 mg of dextroamphetamine sulfate administered about every 4–6 hours during the day and up to about 5 mg during the night if needed for a period of about 5–14 days.

58. The method of claim 45, wherein said effective amount of said at least one anxiolytic agent is about 50–60 mg of chlordiazepoxide administered about every 6–8 hours around the clock initially and gradually tapering said chlordiazepoxide thereafter;
   said effective amount of said at least one centrally acting alpha antiadrenergic agent is about 0.05–0.7 mg of clonidine administered about every 6–8 hours; and
   said effective amount of said at least one central nervous system stimulant is about 1–20 mg of said dextroamphetamine sulfate in a sustained release form administered from about every twelve hours to about once daily for a period of about 5–14 days.

59. The method of claim 45, wherein said effective amount of said at least one anxiolytic agent is about 0.25–10 mg of lorazepam administered about every 6–8 hours during the day and about every 3–4 hours during the night initially, and gradually tapering said lorazepam thereafter;

said effective amount of said at least one centrally acting alpha antiadrenergic agent is about 0.05–0.7 mg of clonidine administered about every 6–8 hours; and said effective amount of said at least one central nervous system stimulant is about 1–20 mg of dextroamphetamine sulfate administered about every 4–6 hours during the day and up to about 5 mg during the night if needed for a period of about 5–14 days.

60. The method of claim 45, wherein said effective amount of said at least one anxiolytic agent is about 0.25–10 mg of lorazepam administered about every 6–8 hours during the day and about every 3–4 hours during the night initially, and gradually tapering said lorazepam thereafter;

said effective amount of said at least one centrally acting alpha antiadrenergic agent is about 0.05–1.4 mg of clonidine about every 6–8 hours; and said effective amount of said at least one central nervous system stimulant is about 1–20 mg of dextroamphetamine sulfate in a sustained release form administered from about every 12 hours to about once daily for a period of about 5–14 days.

61. The method of claim 45, wherein said effective amount of said at least one anxiolytic agent is about 0.25–10 mg of lorazepam administered about every 6–8 hours during the day and about every 3–4 hours during the night initially, and gradually tapering said lorazepam thereafter;

said effective amount of said at least one centrally acting alpha antiadrenergic agent is about 0.05–0.7 mg of clonidine about every 6–8 hours; and said effective amount of said at least one central nervous system stimulant is about 50–400 mg of modafinil administered from about every 12 hours to about once daily for a period of about 5–14 days.

62. The method of claim 45, wherein said effective amount of said at least one anxiolytic agent is about 50–60 mg of chlordiazepoxide administered about every 6–8 hours around the clock initially, and gradually tapering said chlordiazepoxide thereafter;

said effective amount of said at least one centrally acting alpha antiadrenergic agent is about 0.05–0.7 mg of clonidine about every 6–8 hours; and said effective amount of said at least one central nervous system stimulant is about 50–400 mg of modafinil administered from about every 12 hours to about once daily for a period of about 5–14 days.

63. The method of claim 45, wherein said effective amount of said at least one anxiolytic agent is about 0.25–10 mg of lorazepam administered about every 6–8 hours during the day and about every 3–4 hours during the night initially, and gradually tapering said lorazepam thereafter;

said effective amount of said at least one centrally acting alpha antiadrenergic agent is about 0.05–0.7 mg of clonidine about every 6–8 hours; and said effective amount of said at least one central nervous system stimulant is about 1–20 mg of dextroamphetamine sulfate administered about every 4–6 hours during the day and up to about 5 mg during the night if needed; and about 50–400 mg of modafinil administered from about every 12 hours to about once daily for a period of about 5–14 days.

64. The method of claim 45, wherein said effective amount of said at least one anxiolytic agent is about 50–60 mg of chlordiazepoxide, administered about every 6–8 hours around the clock initially, and gradually tapering said chlordiazepoxide thereafter;

said effective amount of said at least one centrally acting alpha antiadrenergic agent is about 0.05–0.7 mg of clonidine administered about every 6–8 hours; and said effective amount of said at least one central nervous system stimulant is about 1–20 mg of dextroamphetamine sulfate administered about every 4–6 hours during the day and up to about 5 mg during the night if needed; and about 50–400 mg of said modafinil administered from about every 12 hours to about once daily for a period of 5–14 days.

65. The method of claim 45, wherein said effective amount of said at least one anxiolytic agent is about 50–60 mg of said chlordiazepoxide, administered about every 6–8 hours around the clock initially, and gradually tapering said chlordiazepoxide thereafter; said effective amount of said at least one centrally acting alpha antiadrenergic agent is about 0.05–0.7 mg of clonidine administered about every 6–8 hours; and said effective amount of said at least one central nervous system stimulant is about 1–20 mg of dextroamphetamine sulfate in a sustained release form administered once daily or about every 12 hours, and about 50–400 mg of modafinil administered about every 12 hours to about once daily for a period of 5–14 days.

66. The method of claim 45, wherein said effective amount of said at least one anxiolytic agent is about 0.25–10 mg of lorazepam administered about every 6–8 hours during the day and about every 3–4 hours during the night initially, and gradually tapering said lorazepam thereafter; said effective amount of said at least one centrally acting alpha antiadrenergic agent is about 0.05–0.7 mg clonidine administered about every 6–8 hours; and said effective amount of said at least one central nervous system stimulant is about 1–20 mg of dextroamphetamine sulfate in a sustained release form administered once daily or about every 12 hours; and about 50–100 mg modafinil administered about every 12 hours to about once daily for period of about 5–14 days.

67. The method of claim 45, wherein said effective amount of said at least one anxiolytic agent comprises gabapentin administered in an amount of from about 300–4000 mg per day.

* * * * *

UNITED STATES PATENT AND TRADEMARK OFFICE
CERTIFICATE OF CORRECTION

PATENT NO.   : 6,417,184 B1
DATED         : July 9, 2002
INVENTOR(S)  : David M. Ockert It is certified that error appears in the above-identified patent and that said Letters Patent is hereby corrected as shown below:

Column 7,
Line 3, "prorate" should be --pamoate --.

Column 15,
Line 7, "0.05-7 mg" should be -- 0.05-0.7 mg --.

Column 18,
Line 6, "0.05-7 mg" should be -- 0.05-0.7 mg --.
Line 30, "thereofl" should be -- thereof --.

Signed and Sealed this

Seventh Day of January, 2003

JAMES E. ROGAN
*Director of the United States Patent and Trademark Office*